(12) United States Patent
Chattopadhyay et al.

(10) Patent No.: US 8,420,100 B2
(45) Date of Patent: Apr. 16, 2013

(54) TUMOR SUPPRESSOR ACTIVATING POLYPEPTIDES AND USES THEREOF

(75) Inventors: Samit Chattopadhyay, Pune (IN); Archana Jalota-Badhwar, Pune (IN)

(73) Assignees: Department of Biotechnology, New Delhi (IN); National Centre for Cell Science, Pune (IN)

( * ) Notice: Subject to any disclaimer, the term of this patent is extended or adjusted under 35 U.S.C. 154(b) by 300 days.

(21) Appl. No.: 12/521,665

(22) PCT Filed: Sep. 10, 2007

(86) PCT No.: PCT/IN2007/000402
§ 371 (c)(1), (2), (4) Date: Nov. 10, 2010

(87) PCT Pub. No.: WO2008/081466
PCT Pub. Date: Jul. 10, 2008

(65) Prior Publication Data
US 2011/0046342 A1      Feb. 24, 2011

(30) Foreign Application Priority Data

Dec. 29, 2006 (IN) .............................. 2835/DEL/06

(51) Int. Cl.
*C12P 21/00* (2006.01)
*A61P 35/00* (2006.01)

(52) U.S. Cl.
USPC ................. 424/192.1; 435/69.5; 514/19.3

(58) Field of Classification Search .............. None
See application file for complete search history.

(56) References Cited

U.S. PATENT DOCUMENTS 5,804,604 A * 9/1998 Frankel et al. ................ 530/324

OTHER PUBLICATIONS

Jalota et al., "Tumor Suppressor SMAR1 Activates and Stabilizes p53 through Its Arginine-Serine-rich Motif", J. Biol. Chem., 2005; 280(16); pp. 16019-16029.
Friedler et al., *Development of a Functional Backbone Cyclic Mimetic of the HIV-1 Tat Arginine-rich motif*, J. Biol. Chem., 2000, 275(31); pp. 23783-23789.
Kaul et al., "Direct interaction with and activation of p53 by SMAR1 retards cell-cycle progression at $G_2/M$ phase and delays tumor growth in mice", Int. J. Cancer, 2003, 103(5); pp. 606-615.
Jolota-Badhwar et al., "SMAR1-derived P44 peptide retains its tumor suppressor function through modulation of p53", J. Biol. Chem., 2007, 282(13); pp. 9902-9913.
Kaul-Ghanekar et al., "Abnormal V(D)J Recombination of T Cell Receptor β Locus in SMAR1 Transgenic Mice", J. Biol. Chem., 2005, 280(10), pp. 9450-9459.

* cited by examiner

*Primary Examiner* — Elly-Gerald Stoica
(74) *Attorney, Agent, or Firm* — Venable LLP; Nancy J. Axelrod; Keith G. Haddaway

(57) ABSTRACT

Chimeric tumor suppressor activating peptides derived from matrix attachment region binding protein (MARBP) SMAR1 unique in their sequence comprising a arginine rich motif flanked by serine residues wherein from the stretch of four consecutive serine residues the first serine residue gets phosphorylated by the protein kinase C family of serine threonine kinases being indispensable for its functionality, the phosphorylation being directly correlated to the phosphorylation of p53 at serine 15 residue thereby stabilizing it, wherein the peptide activates p53 by modifying it post translationally which allow phosphorylation and translocation of p53 to the nucleus.

2 Claims, 8 Drawing Sheets

TUMOR SUPPRESSOR ACTIVATING POLYPEPTIDES AND USES THEREOF

Figures 1A, 1B, 1C, 1D, 1E, 1F, 1G, 1H:
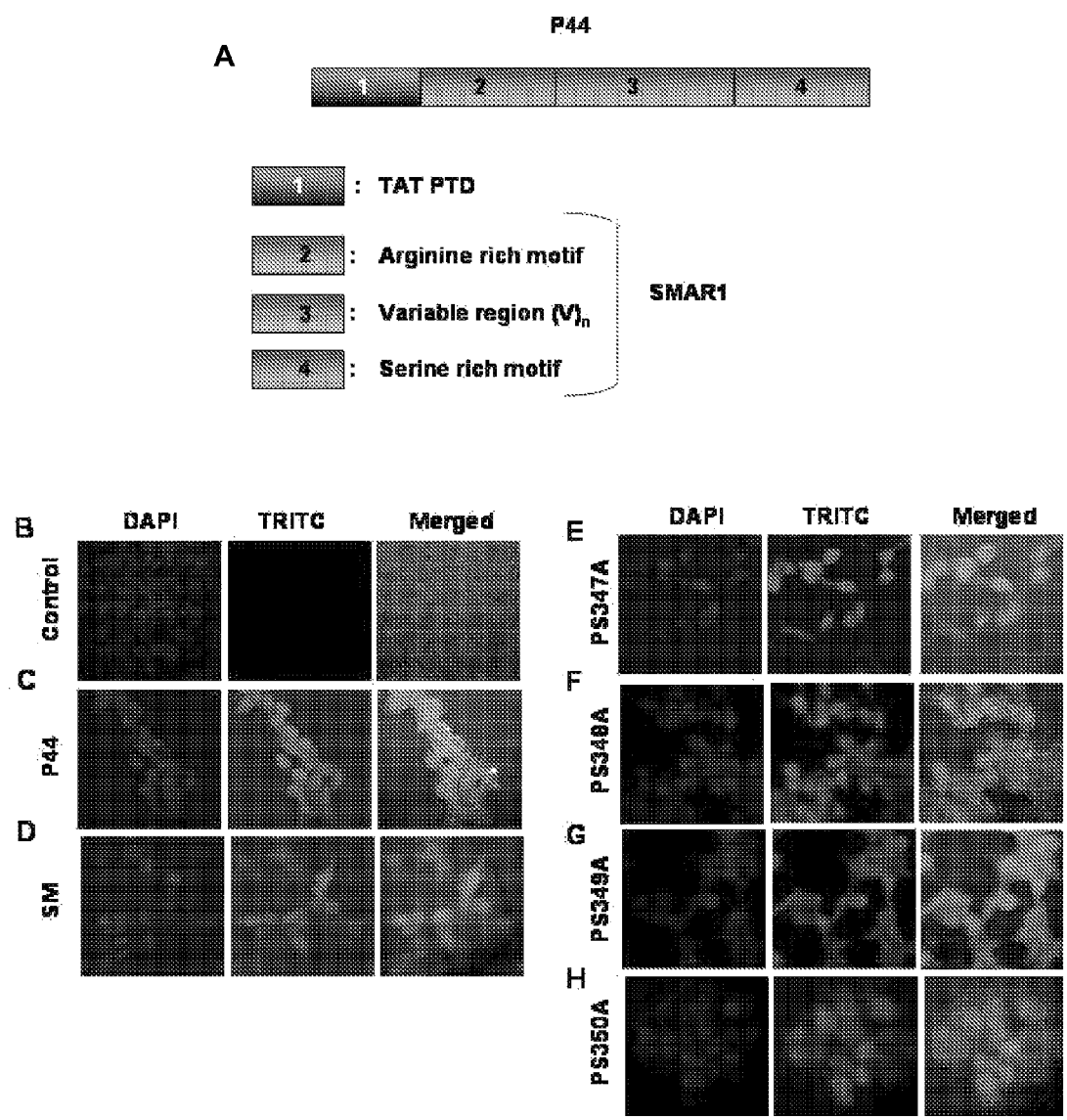

This application is a National Stage Application of International Application No. PCT/IN07/00402, filed Sep. 10, 2007, which claims priority to Indian Patent Application No. 2835/DEL/06, filed Dec. 29, 2006, each of which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Aug. 8, 2012, is named 31446278.txt and is 7,379 bytes in size.

FIELD OF INVENTION

This invention relates to an active peptide derived from a protein that interacts with p53 antitumor factor and activates, leading to suppression of neoplastic growth.

BACKGROUND OF THE INVENTION

Despite tremendous efforts in molecular, biochemical and cell biological research towards understanding the intra- and extra-cellular mechanisms involved in the transformation of a normal cell into a cancerous one, the number of successful treatments against cancer is few. A major limitation of cancer therapeutics is the problem of delivering pharmacologically relevant compounds, peptidyl mimetics, antisense oligonucleotides, and proteins into cells (Egleton, R. D., and Davis, T. P. (1997) Peptides 18, 1431-1439). Peptide-based drugs have limitations in the form of the poor permeability and selectivity of the cell membrane. These problems are now circumvented by attaching protein translocation domains (PTDs) to the peptides that, can cross the biological membranes efficiently without any dependence on transporters or specific receptors and mediate the intracellular delivery of a range of biological cargos (Schwarze, S. R., Hruska, K. A., and Dowdy, S. F. (2000) Trends Cell Biol. 10, 290-295; Ford, K. G., Souberbielle, B. E., Darling, D., and Farzaneh, F. (2001) Gene Ther. 8, 1-4). The PTD of HIV-1 Tat protein in well-known to mediate transduction of heterologous peptides and biologically active proteins in vitro and in vivo (Ho, A., Schwarze, S. R., Mermelstein, S. J., Waksman, G., and Dowdy, S. F. (2001) Cancer Res. 61, 474-477) and thus has been shown to be of considerable interest for protein therapeutics (Schwarze, S. R., Ho, A., Vocero-Akbani, A., and Dowdy, S. F. (1999) Science 285, 1569-1572).

The integrity of the eukaryotic genome requires several layers of control to ensure that replication of DNA occurs only once during a cell cycle (Elledge, S. J. (1996) Science 274, 1664-1672). For normal cellular functions and tissue homeostasis, accurate transmission of genetic information between generations is required. Dysregulation of the cell cycle control is a hallmark of cancer (Hanahan, D., and Weinberg, R. A. (2000) Cell 100, 57-70). Neoplastic progression has been demonstrated to involve increased genetic instability (Donehower, L. A. (1997) Cancer Surv. 29, 329-352; Harley, C. B., and Sherwood, S. W. (1997) Cancer Surv. 29, 263-284) and there are enough reports revealing that the disruption of multiple pathways is required for the development of cancer (Hunter, T. (1997) Cell 88, 333-346). Inactivation or loss of p53 is a common event associated with the development of approximately 60% of all human cancers (Levine, A. J. (1997) Cell 88, 323-331; Michael, D., and Oren, M. (2002) Curr. Opin. Genet, Dev. 12, 53-59). The tumor suppressor protein p53 is a short lived, latent transcription factor that is activated and stabilized in response to a wide range of cellular stresses, including DNA damage and activated oncogenes. p53 has been shown to participate in the regulation of several processes, which might inhibit tumor growth, including differentiation, senescence and angiogenesis (Vogelstein, B., Lane, D., and Levine, A. J. (2000) Nature 408, 307-310; Oren, M. (2003) Cell Death, Differ. 10, 431-442). However, central to the function of p53 appears to be the ability to induce both cell cycle arrest and/or apoptosis in stressed cells, partly by activating expression of p53 responsive target genes that mediate these responses (Ashcroft, M., Taya, Y., and Vousden, K. H. (2000) Mol. Cell. Biol. 20, 3224-3233; Woods, D. B., and Vousden, K. H. (2001) Exp. Cell Res. 264, 56-66). Since p53 maintains the genetic stability, it must be under rigorous and complex control. Highly conserved residues in its N- and C-terminal domains are targets for potential post-translational modification via phosphorylation, ubiquitination or acetylation (reviewed by Giaccia and Kastan, 1998: Michael, D. and M. Oren. 2003. Semin. Cancer Biol. 13:49-58). The precise mechanism of p53 activation by cellular stress is of intense interest and may involve both increase in p53 protein level and in the specific activity of p53 by covalent modifications (Harris. S. L., and Levine, A. J. (2005) Oncogene 24, 2899-2908.

The present investigations were aimed at using the protein translocation domain (PTD) of Tat protein to deliver short peptide sequences of tumor suppressor protein SMAR1 both in vitro and in vivo. SMAR1, a recently identified MARBP, was isolated from double positive mouse thymocytes (Chattopadhyay et al., 2000, Genomics). SMAR1, a 68 KDa protein has been previously shown to interact with p53 (Jalota et al., 2005). SMAR1 exists in two alternatively spliced forms: SMAR1$^L$ and SMAR1$^S$, with deletion of 39 amino acids in the N-terminus and shares approximately 99% homology with its human homolog, BANP (Birot et al., 2000 Gene 253, 189-196). Interestingly, in numerous cancers, altered expression of several MAR binding proteins have been demonstrated (Liu, W et al., (1999) Cancer Res. 59:5695-5703). In the present work, we show that a 33-mer SMAR1 peptide conjugated to an 11-mer protein transduction domain (PTD) of HIV-1 TAT protein is sufficient enough to inhibit the tumor growth in nude nice. Exposure of cells to this peptide resulted in increased p53 phosphorylation at its serine 15 residue, in turn, activating the p53-mediated cell cycle control. Point-mutation studies of P44 peptide further revealed that the serine 347 residue within the serine-rich motif of SMAR1 plays a pivotal role in mediating the tumor suppressor effect of SMAR1. The 347 serine residue represents the substrate motif for the PKC family of proteins and its phosphorylation is necessary for activating the p53-dependent pathway. We also observe that tumors excised from mice treated with SM mutant peptide showed leaky vascular architecture compared to P44 treated tumors. Interestingly, there was no detectable level of HIF-1α in tumors from mice treated with SMAR1 peptide that is a hallmark of tumor hypoxia. Thus, our results implicate that this SMAR1 peptide can be used, as an alternative drug for cancer therapy.

Major research efforts are aimed at discovery of molecular targets that are specific as well as toxic to cancer cell. Identification of potential targets for therapeutic intervention thus fuels a hope for curing cancer. Peptide-mediated molecular therapeutic delivery systems have currently emerged as an alternative means to effectively substitute or augment present gene therapy technologies, e.g. TAT, VP22, engineered peptides. This invention potentiates the use of P44 peptide of SMAR1 for peptidometic cancer drug design so as to allow therapeutic intervention in the target cell biochemistry without the need to alter its genome.

Inactivation or loss of p53 is a common event associated with the development of approximately 60% of all human cancers. p53 has been shown to participate in the regulation of several processes which might inhibit tumor growth, including differentiation, senescence and angiogenesis. However, central, to the function of p53 appears to be the ability to induce cell cycle arrest and/or apoptosis in stressed cells, at least in part by activating expression of p53-responsive target genes that mediate these responses. Recently, Inventors have identified a novel peptide derived from MAR binding protein; SMAR1 that regulates cell cycle through modulating the activity of p53 and acts as a potent tumor regressor.

OBJECTS OF THE INVENTION

The object of the invention is to generate an active peptide that interacts with anti-tumor factor.

Other object is to generate an active peptide from a protein that interacts with p53 anti-tumor factor.

Further object is to produce shorter peptide of tumor suppressor protein SMAR1 that retains the potential to activate and stabilize p53 as much as the full length protein.

Yet another object is to evaluate the functionality of the peptide with respect to activation of p53 and p53-target genes.

Other object is to generate its mutant and to further identify the residue indispensable for its activity.

Further object of this invention is to use the active peptide for suppression of neoplastic growth.

Yet another objective is to use P44 peptide of SMAR1 for peptidometic cancer drug design to allow therapeutic intervention in the target cell biochemistry without the need to alter its genome.

DETAILED DESCRIPTION OF THE INVENTION

New revelations continue to emerge concerning the mechanisms that control p53 activation in response to a wide range of input signals. Diverse stimuli appear to invoke similar set of responses to achieve p53 activation: p53 must first accumulate in the nucleus, and then bind to DNA as a tetramer to transcriptionally regulate a growing list of target genes including p21, GADD45, 14-3-3-sigma, MDM2, IGF-BP3, cyclin G and bax (reviewed E1-Deiry, 1998: Oren, 2003). In the absence of stress, p53 is maintained at very low steady-state levels, and is thus prevented from exerting profound, effects on the cell phenotype. Multiple lines of evidence indicate that the lion's share of the negative regulation of p53, under nonstressed conditions, is performed by the Mdm2 protein (Michael and Oren, 2002: Daujat et al., 2001). Mdm2 binds at the N-terminal transactivation domain of p53 and blocks the critical interactions with other proteins necessary for p53 dependent gene regulation. It plays a cardinal role in the ubiquitnation-mediated proteasomal degradation of p53 under nonstressed conditions.

Various p53-modulating proteins have been identified so far that results in p53 activation in a DNA damage dependent manner (Banin et al., (1998) Science 281: 1674-1677; Zheng et al., (2002) Nature 419:849-853). We have reported another p53 interacting protein, SMAR1 (Scaffold/Matrix Associated Region). SMAR1, a recently identified MARBP, was isolated from double positive mouse thymocytes, (Chattopadhyay et al., 2000). It specifically binds to a putative MAR (MARβ), a DNase I-hypersensitivity site located 400 bp upstream of the transcriptional enhancer (Eβ) at the T-cell β locus. SMAR1 exists in two alternatively spliced forms: SMAR1$^L$ and SMAR1$^S$, with deletion of 39 amino acids in the N-terminus. The SMAR1 gene maps to the distal portion of mouse chromosome 8 at a distance of 111.8 cM. Interestingly, in numerous cancers, altered expression of several MAR Binding proteins have been demonstrated. Both we-p53 and mutant p53 have also been shown to bind to the nuclear matrix (Jiang et al., (2001) Oncogene 20: 5449-5458). However mutant p53 binds with high affinity to variety of MAR-DNA elements resulting in base unpairing (Appella and Anderson, (2000) Pathol. Biol. (Paris) 48:227-245).

Figures 1I, 1J, 1K, 1L:
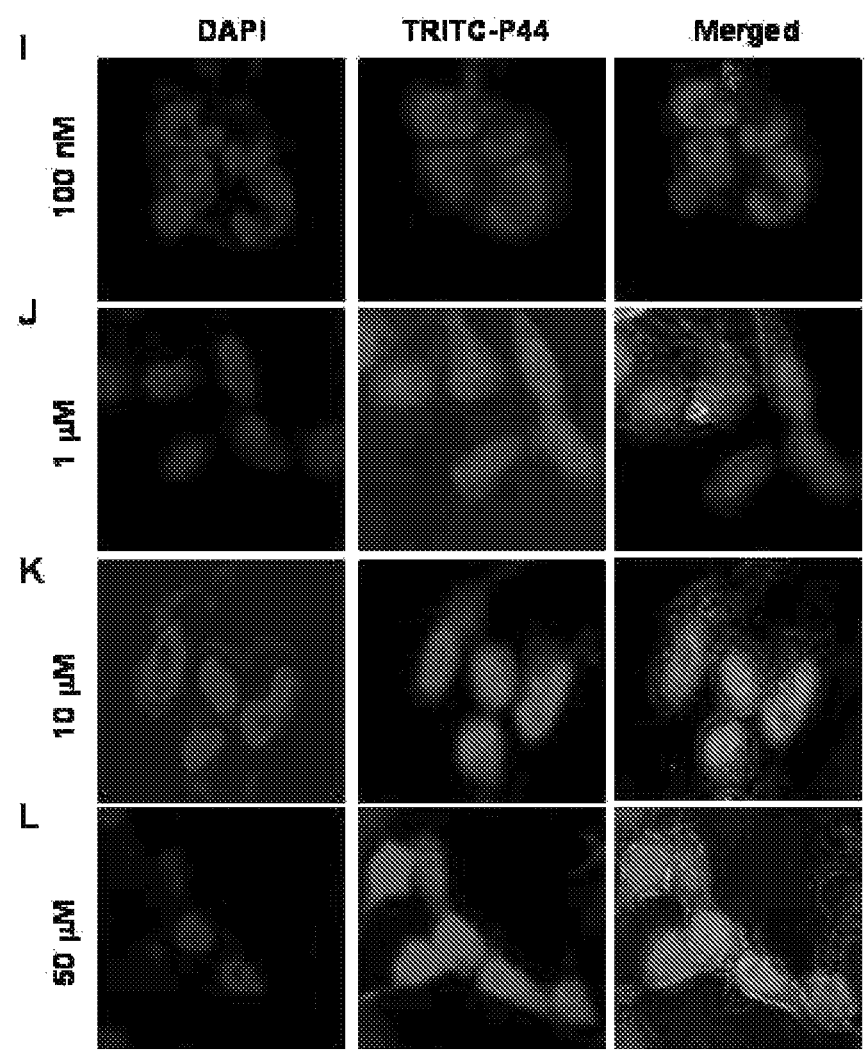

Uptake the nuclear compartmentalization of chimeric TAT PTD-SMAR1 derived peptides: Since the amino acids 288-350 play a critical role in p53 modulation (30) and in turn cell cycle regulation, we commercially synthesized shorter SMAR1 derived peptides to evaluate their efficacy in vitro and in vivo. Several reports have established that the chemical conjugation of the protein transduction domain (PTD) derived from HIV-1 TAT protein was able to induce cellular internalization of large proteins such as β-galactosidase or horseradish peroxidase (Fawell, S (1994) Proc. Natl. Acad. Sci. U.S.A. 91, 664-668; Vocero-Akbani (2001) Methods Enzymol. 332, 36-49). With the prospect of using similar tools for drug delivery, it was of interest to design SMAR1-derived peptide and explore its mechanism of internalization. A 33 mer peptide sequence extending from residues 324-357 aa was conjugated with 11-mer TAT-PTD and designated as TAT-SMAR1 WT (P44). This short peptide sequence overlapped with the PKC substrate motif (the serine rich motif) of the full-length SMAR1, known to be involved in its phosphorylation and subsequent nuclear accumulation of p53. Various serine-mutants, where serine was replaced by alanine, of the P44 peptide (PS347A, PS348A, PS349A, and PS350A) and SMAR1 RS mutant (SM), were also commercially synthesized (FIG. 1A; Table 1). To understand the mechanism of uptake and intracellular compartmentalization of all these peptides, they were labeled with TRITC fluorochrome and purified using PD-10 column. Upon exposure of cells to either of the peptides, except the control (FIG. 1B), all others were observed to get localized into the nucleus (FIG. 1C-H). Internalization of all TAT-SMAR1 chimeric peptides within the nucleus occurred in a dose-dependent manner (data shown only for P44 peptide) (FIG. 1I L) as observed by the intensity of the recorded signal. At a concentration of around 50 μM (that seemed to be saturating), TRITC-labeled peptides could also be detected in the cytoplasm (FIG. 1L). There was no overall variation in the uptake and localization between the various SMAR1-derived TAT conjugated peptides (FIG. 1C-H). A non TAT conjugated SMAR1 peptide labeled with TRITC was used as negative control which as expected, was not taken up the cells as recorded with no fluorescent signal (FIG. 1B). The results thus confirmed that the chimeric peptides of SMAR1 were efficiently translocated into the nucleus by TAT PTD.

Figures 2A, 2B:
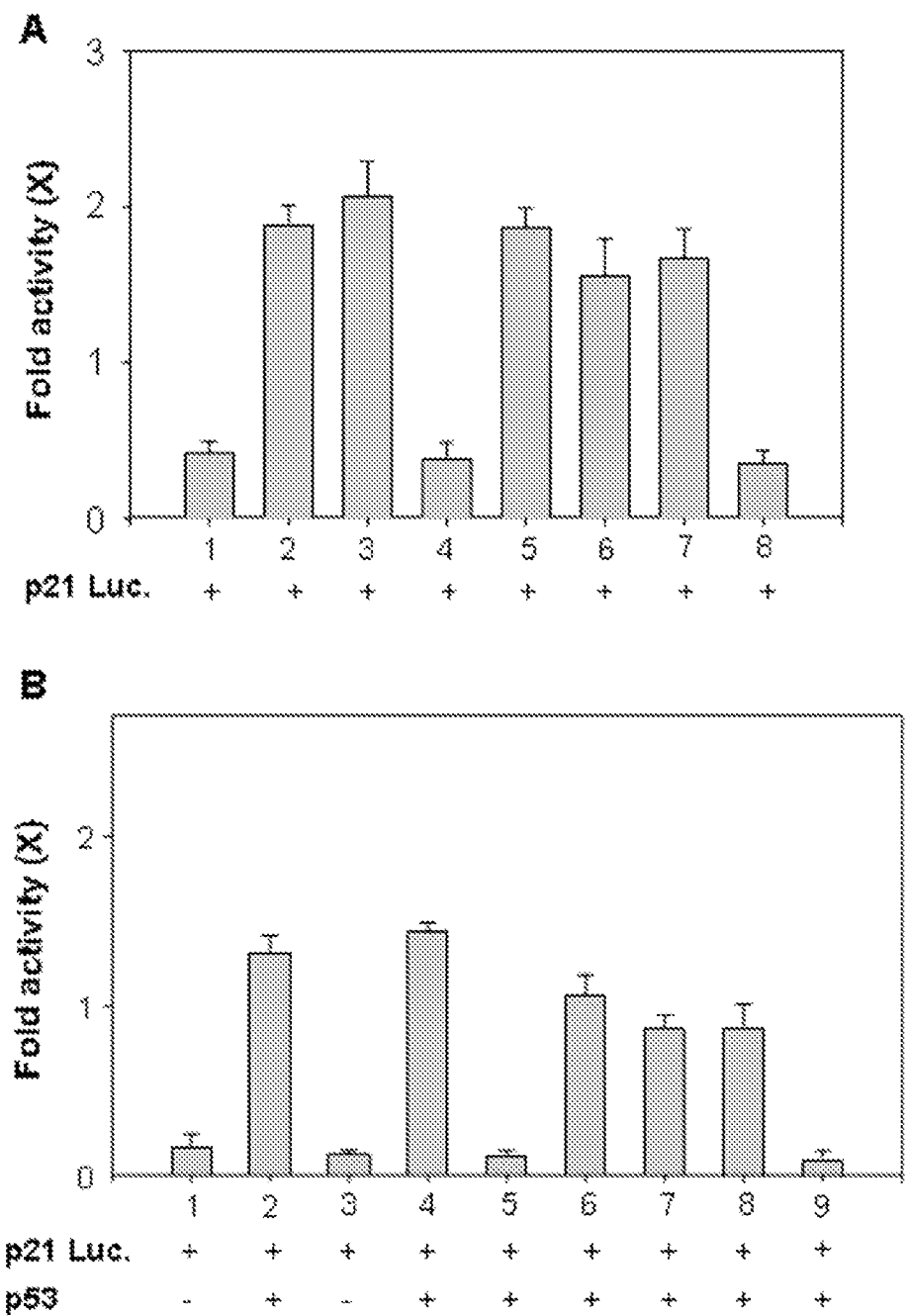
Figures 3A, 3B, 3C, 3D:
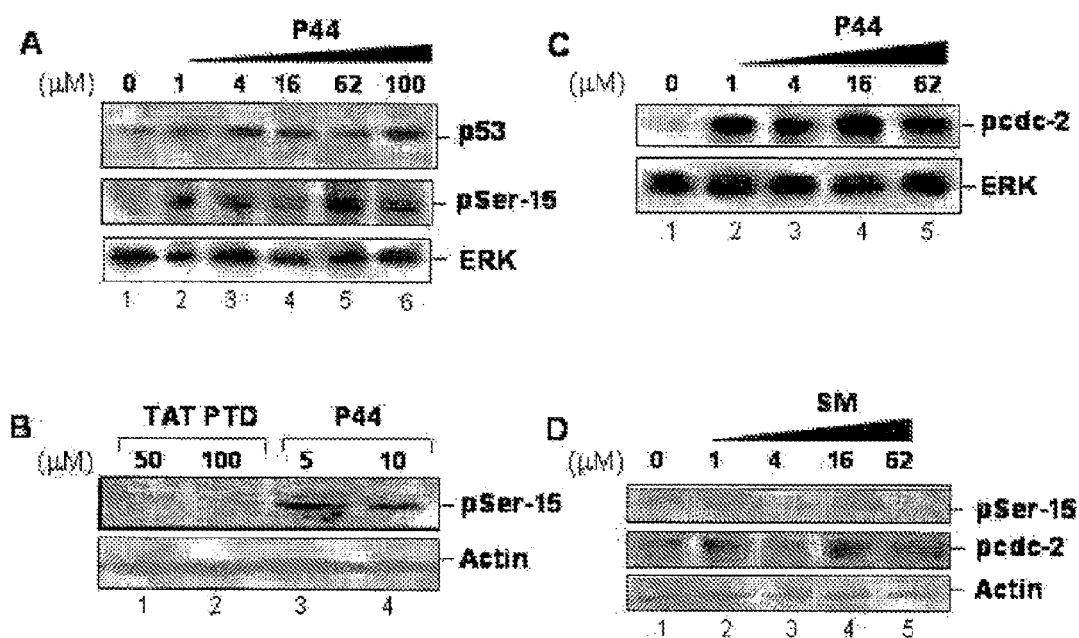

TAT-SMAR1 WT peptide (P44) modulates p53 function: To examine whether P44 peptide could alone activate p53$^-$, luciferase reporter assays were performed following treatment of cells with the chimeric TAT-SMAR1 derived peptides. HEK 293 (p53$^{+/+}$) cells were transfected with p21 expression plasmid having luciferase reporter gene and K562 (p53$^{-/-}$) cells were co-transfected with p21 luciferase reporter and p53 constructs. Treatment of cells with 10 μM of P44 peptide resulted in a 2-fold activation of p53 in p53$^{+/+}$. (FIG. 2A, bar 3) and about 1.5 fold activation in p53$^{-/-}$ cell line (FIG. 2B, bar 4). In the presence of P44 peptide alone, there was no activity in p53$^{-/-}$ cells indicating that peptide itself does not transactivate the p53 responsive p21 promoter (FIG. 2B, bar 3). However, point mutation at serine 347 residue (PS347A) as well as the SMAR1 RS mutant peptide (SM) resulted in complete loss of p21 promoter driven luciferase activity in both p53 WT and p53 null cell lines (FIG. 2A, bars 4 and 8; FIG. 3B, bars 5 and 9, respectively). No significant alteration in activation of p53 was observed by peptides with point mutations at serine 348 (PS348A), serine 349 (PS349A) or serine 350 residue of SMAR1 (PS350A) (FIG. 2A, bars 5-7; FIG. 2B, bars 6-8). Thus, these results indicate that serine-347 residue within the RS domain (288-350 aa) of SMAR1 is necessary for modulating p53 activity.

P44 peptide controls the activity of cell cycle regulatory proteins: The minimal dose of P44 peptide that was functionally effective in activating p53 was evaluated by incubating HEK 293 cells with varying concentrations of P44 peptide (1-100 μM) (FIG. 3A) and after 12 h of incubation, protein lysates were prepared and processed for immunoblotting with total p53 (DO-1) and p53 ser-15 phospho-specific antibodies. A slight increase in the total p53 expression was observed. However, there was a 4.5-fold increase in the expression of phosphorylated p53 (pSerine-15 p53) in P44 peptide-treated cells (FIG. 3A, lanes 2-6). To exclude the possibility that p53 activation is an effect of the protein transduction domain of HIV-1 TAT protein, similar set of experiment was performed using TAT-PTD peptide alone (consisting of only the 11-mer TAT-sequence). As expected, no phosphorylation of serine-15 residue of p53 was observed in TAT-treated cells, although when used at a much higher concentration (50-100 μM) (FIG. 3B, lanes 1 and 2) with respect to P44 peptide (5-10 μM) (FIG. 3B, lanes 3 and 4). This observation reconfirmed that the RS domain (288-350 aa) of SMAR1 could exclusively activate p53 by mediating its phosphorylation specifically at serine-15 residue. Serine-15 phosphorylation of p53 is associated with its increased transcription efficiency, decreased affinity for MDM2, and its increased nuclear retention. One of the target genes activated by p53 is p21, an inhibitor of a subset of the cyclin-dependent kinases including cdc-2 (Sherr, C. J., and Roberts, J. M. (1999) Genes Dev. 13, 1501-1512). To evaluate the significance of peptide-mediated p53 activation, P44 peptide-treated lysates were further checked for tyrosine 15 phosphorylation of cdc2. Membrane immunoblotted with pcdc-2 antibody showed upregulation of pcdc-2 (FIG. 3C, lanes 2-5) in comparison to only cells (FIG. 3C, lanes 1), again confirming that P44 peptide was capable enough to mediate the effects of full-length SMAR1 and thus it may possess the entire functional activity to regulate the cell cycle. No changes were observed in the total ERK levels that were used as a loading control. TAT-SMAR1 RS-mutant peptide (SM) was further used to demonstrate that the serine motif (SSSSYS) of SMAR1 minimal domain (arginine-serine rich) is essential for mediating the effects of full-length SMAR1 in p53 activation signaling. HEK 293 cells were treated with SM peptide and checked for p53 as well as pcdc-2 levels. The SM peptide-treated lysates showed no increase both in the expression levels of p53 phospho-serine 15 or pcdc-2 levels when compared to untreated cells (FIG. 3D).

Figures 4A, 4B, 4C, 4D, 4E, 4F, 4G:
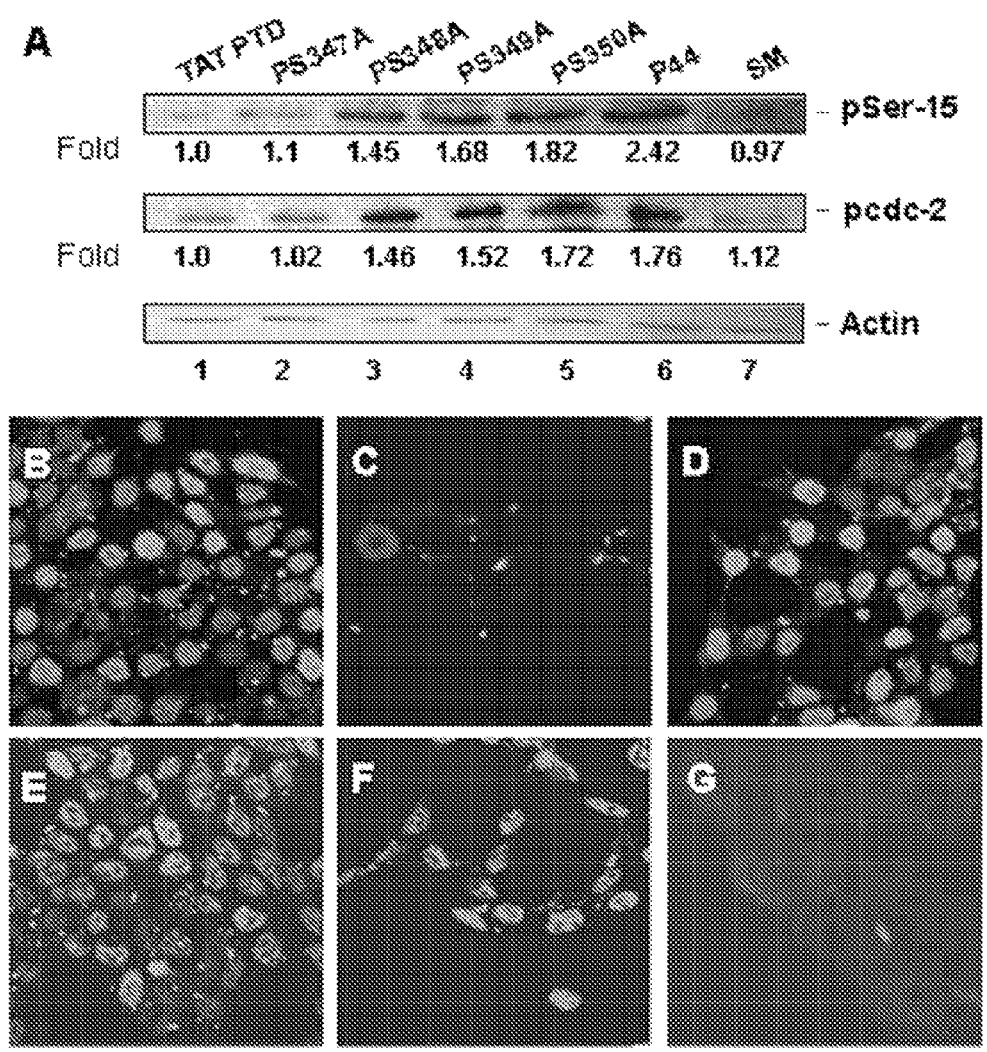

Serine 347 residue of SMAR1: critical for mediating the effects of full-length SMAR1: Once it was established that the serine motif (SSSSYS) plays a pivotal role in SMAR1-mediated p53 activation, it got necessary to identify the serine residue within this motif that might be necessary in mediating these effects. To identify the critical serine residue within P44 peptide, various point-mutant peptides were custom synthesized, that varied with respect to the position of serine residue that was mutated (Table 1). To evaluate the functionality of mutant chimeric TAT-SMAR1 peptides [PS347A, PS348A, PS349A, PS350A and RS mutant (SM)] in comparison to the TAT-SMAR1 WT peptide (P44), HEK 293 cells were treated with 10 μM concentration of either of the peptides and protein lysates were prepared after 12 h incubation period. The lysates were then processed for immunoblotting with pSer-15 p53 and pcdc-2 antibodies. Inventors observed that when the first serine residue of P44 peptide was replaced with alanine (PS347A), there was no significant activation of p53 (FIG. 4A, lane 2) thus, demonstrating the significance of serine 347 residue of SMAR1. The increase in the pcdc-2 levels that was observed in case of P44 (FIG. 5A, lane 6) was decreased in PS347A treated cells (FIG. 4A, lane 2). However, this was not the case with other mutated peptides. When the alanine was replaced back to serine at the 347 residue (FIG. 4A, lanes 3-5), the functionality of the peptide was restored as observed with increase in pcdc-2 levels. No significant decrease in p53 activation and subsequent increase pcdc-2 was observed between various P44 mutant peptides; PS348A, PS349A and PS350A (FIG. 4A, lanes 3-5). However, in case of SM (where serine residues from 347-350 were replaced by alanines) treated cells (FIG. 4A, lane 7), there was no difference in the pSer-15 p53 as well as pcdc-2 levels compared to either untreated or PS347A treated cells (FIG. 4A, lanes 1 and 2, respectively). These observations strongly suggest that the first serine residue of the SMAR1 serine motif if most critical and essential for SMAR1-mediated p53 activation.

In a similar approach, immunofluorescence studies were performed to demonstrate p53 stabilization upon peptide treatment. HEK 293 cells were treated with 10 μM of various TAT-SMAR1 derived peptides. After 12 h of incubation, cells were indirectly stained for p53 and counterstained with FITC and the expression of p53 was observed with confocal imaging. As demonstrated in our earlier report that SMAR1 overexpression results in increased retention of activated p53 within the nucleus (Jalota, A., Singh, K., Pavithra, L., Kaul-Ghanekar, R., Jameel, S., and Chattopadhyay, S. (2005) J. Biol. Chem. 280, 16019-16029), treatment of cells with P44 peptide also showed a similar effect. The peptide could activate and stabilize p53 within the nucleus (FIG. 4B). However, both PS347A and SM peptide were unable to activate p53, as evident by almost negligible expression of p53 within the nucleus (FIGS. 4C and G, respectively). On the other hand, p53 stabilization was observed in cells treated with PS348A, PS349A or PS350A (FIGS. 4D, E and F, respectively) thereby confirming that the serine 347 residue of SMAR1 was indispensable for SMAR1-mediated p53 activation and hence stabilization.

Figure 5:
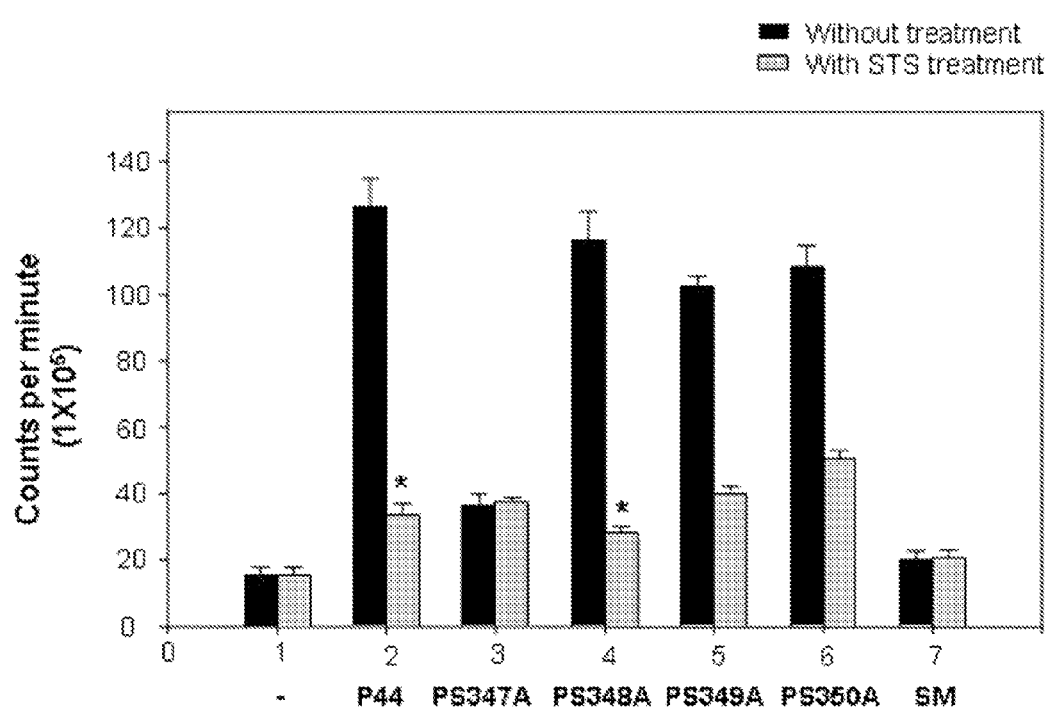

Serine 347: Substrate for PKC family of proteins: Since the P44 peptide could result in a significant increase in P53 ser-15 phosphorylation, an in vitro kinase assay was performed to determine phosphorylation status of P44 peptide. Here the inventors observed that in the presence of whole cell extract from 293 cells enriched with cellular kinases, P44 but not the SM peptide, gets phosphorylated. There was about 6 to 7-fold increased γ-P$^{32}$ ATP incorporation in the wild-type peptide (P44) in comparison to its mutant counterpart (SM) (FIG. 5, dark bars 2 and 7, respectively). P44 phosphorylation was abolished as soon as the serine 347 residue was mutated to alanine (Ps347A) (FIG. 5, dark bar 3). However, phosphorylation was restored with other point mutated peptides (PS348A-PS350A) (FIG. 5, dark bars 4-6, respectively), strongly suggesting that the serine 347 residue of SMAR1 serves as the kinase-targeted molecule. Earlier, Inventors have reported that the protein kinase C (PKC) family of proteins is responsible for post-transcriptional modification of SMAR1 at its arginine-serine rich domain. To further analyse whether the serine 347 residue serves as a substrate motif, specifically for PKC, whole cell extract froth staurosporine (STS) (a PKC inhibitor) treated 293 cells was used for performing in vitro phosphorylation assays with various TAT-SMAR1 peptides. As expected, due to inhibition of PKC, cellular extracts prepared post STS-treatment failed to phosphorylate P44 peptide along with PS348A, PS349A and PS350A peptides (FIG. 5, light bars 2, 4-6, respectively). On the other hand, in case of PS347A and SM peptides, there was no difference in their phosphorylation status with or without STS treatment (FIG. 5, light and dark bars 3 and 7, respectively); thereby confirming that serine 347 residue of SMAR1 serves as the substrate for PKC family.

P44 peptide: A potent tumor regressor: To test whether the differences in SMAR1 derived peptide-induced activation of p53 translated to differences in drug sensitivity in vivo, B16F1 mouse melanoma cells were subcutaneously grafted into athymic nude mice, and tumor growth together with therapeutic sensitivity was monitored. Once the tumor nodule was established into the mouse, P44 peptide was injected in the tumor localized areas at a physiological dose of 200 µg/mouse thrice a week. The treatment was continued for 4 weeks. In a parallel experiment, either TAT PTD or TAT-SMAR1 RS mutant peptide, SM (FIGS. 6A and B, respectively) was injected in tumor bearing mice to be used as control. Interestingly, there was a marked difference in the xenograft's response to the P44 peptide treatment. Almost 5-7 fold regression in tumor was observed in the mice injected with P44 peptide (FIG. 6C) compared to either TAT-injected or SM injected mice.

Figures 6A, 6B, 6C, 6D, 6E, 6F, 6G:
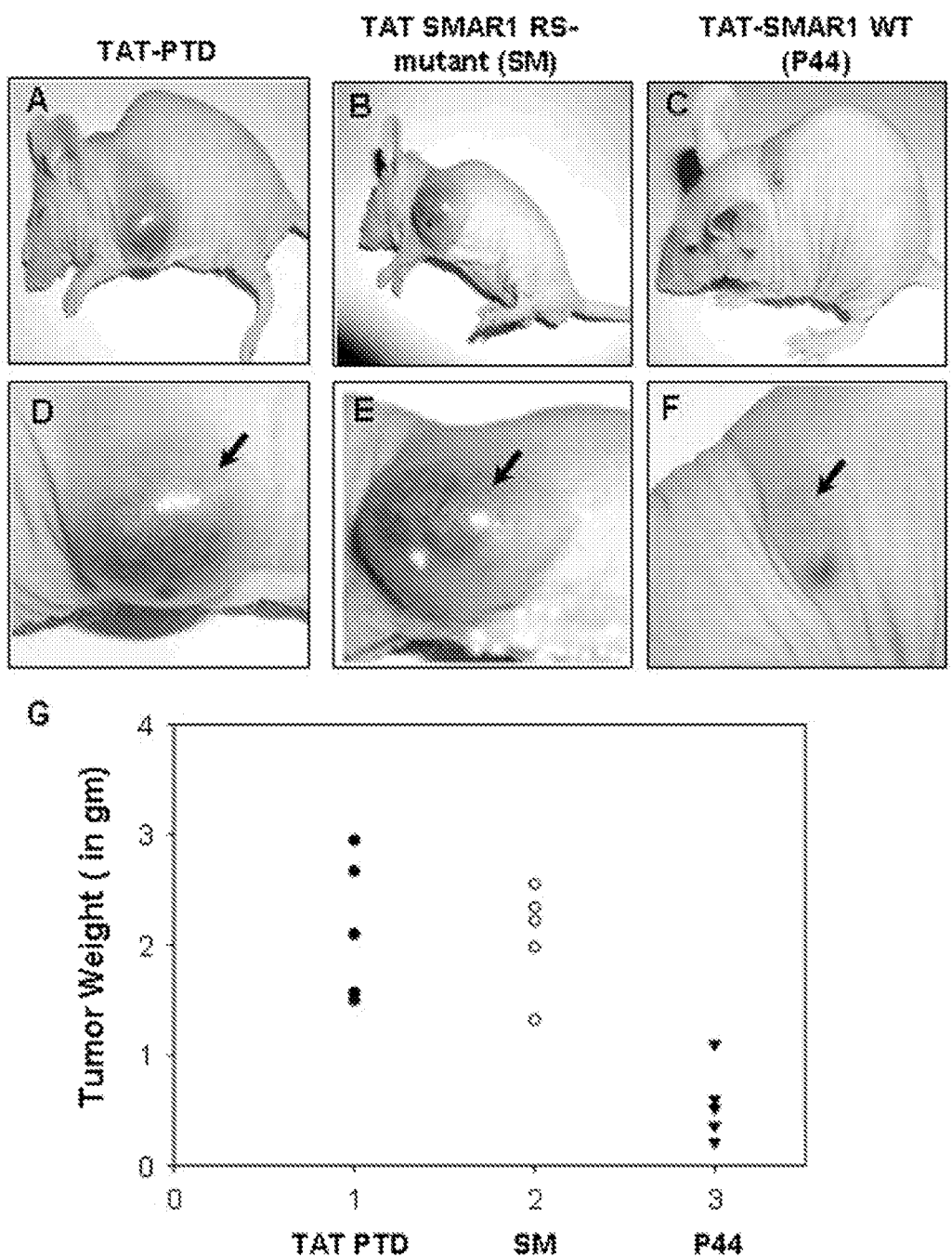

FIG. 6D-F corresponds to the magnified tumor images of FIG. 6A-C, respectively. After excision, the tumor weight was found to be 0.2 g-0.8 g for mice treated with the P44 peptide which was significantly less when compared to the mice treated with either the TAT PTD (1.5-3 G) or SM peptide (1.2-2.5 g) (FIG. 6G). Thus, P44 peptide mimics the function of full-length SMAR1 in drastically reducing the tumor growth.

Figures 7A, 7B:
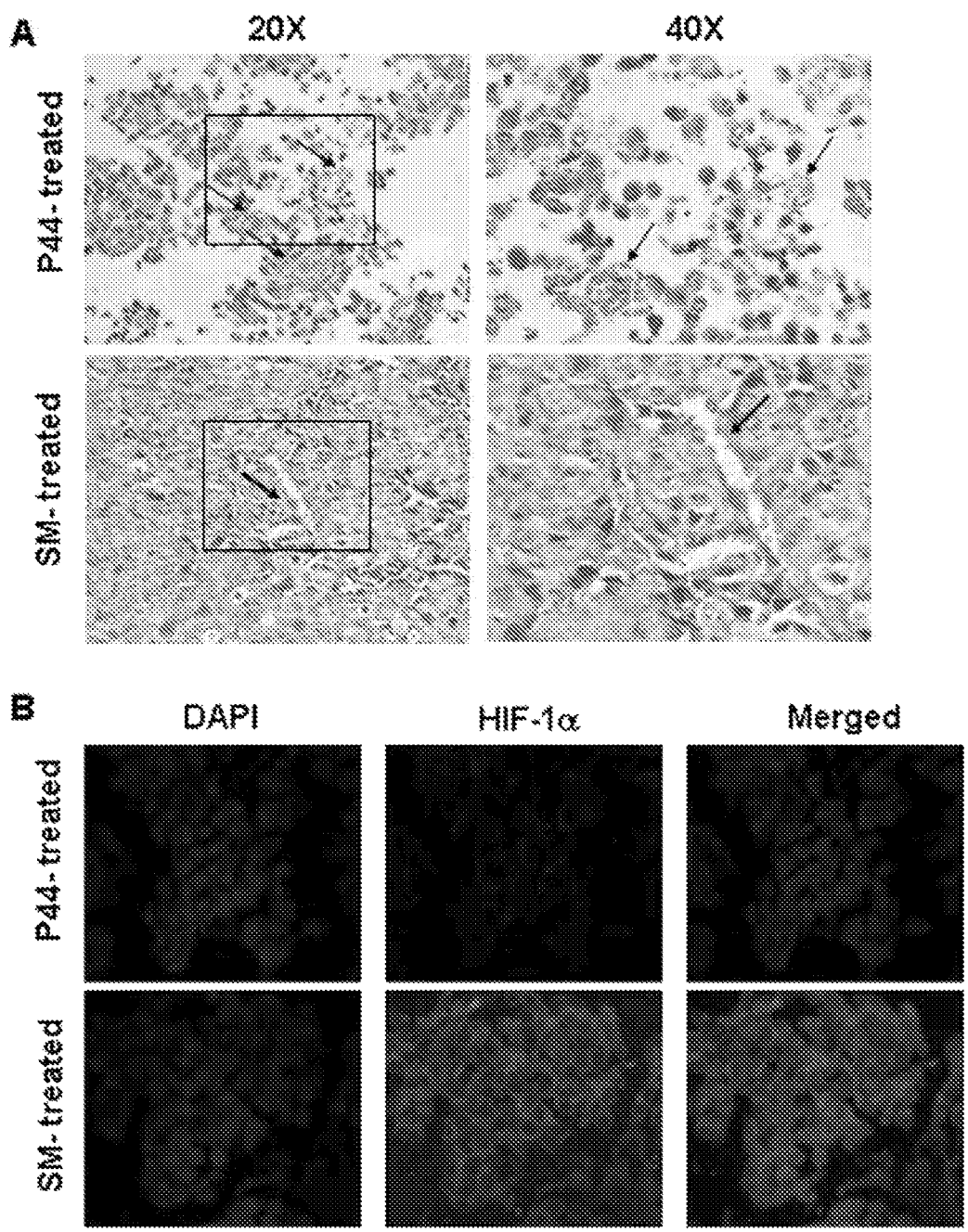

Histopathological changes in the subcutaneous tumors: To analyze the tumor vasculature of TAT PTD, SM treated and P44 treated mice, the tumor sections were stained with HE. Tumors from TAT PTD (data no shown) and SM treated mice exhibited poorly organized vascular architecture and compressed blood vessels due to extensive cell proliferation (FIG. 7A, lower panel). Contrarily, P44 treated tumors showed intact vasculature wherein the RBCs within the vessels were observed in healthy condition (FIG. 7A, upper panel). In SM treated tumors, due to compressed vessels, the shape of RBCs were also distorted (FIG. 7A, lower right panel, arrow marked). Inventors further observed that the inter-vessel distance in P44 treated tumors were significantly less compared to SM-treated tumors (FIG. 7A, upper and lower left panels, respectively). The presence of hypoxic cells is a hallmark of cancer (Brown, J. M., and Wilson, W. R. (2004) Nat. Rev. Cancer 4, 437-447; Minchinton, A. I., and Tannock, I. F. (2006) Nat. Rev. Cancer 6, 583-592). Cellular responses to hypoxia are triggered by the hypoxia inducible factor-1 alpha (HIF-1α) that is known to restore tissue homeostasis in hypoxic conditions (Semenza, G. L. (2000) Genes Dev. 14, 1983-1991). To determine the status of HIF-1α expression, immunohistochemical analysis was performed on tumor sections obtained from SM and P44 treated mice by using antibody against HIF-1 α. Compared to P44 tumor sections, SM sections demonstrated increased HIF-1 α expression (FIG. 7B) thereby resulting into proliferation of tumor cells even under hypoxic conditions. All these observations implicate the significance of P44 peptide in restoring tissue architecture in tumor cells and thus potentiates its role as a tumor regressor.

Interest in peptides and proteins is becoming increasingly important, not only as molecular tools for the understanding of protein-protein interactions, but also as therapeutic compounds. Several oligopeptides such as p53 carboxyl terminal peptide, BH3 domain of Bak, p21WAF1-, p16INK4A-, Sos- and c-Myc derived peptide have been developed as a cargo and proved to function against cancer cells. In vitro studies involving systematic screening of panels of human-tumor derived cell lines for sensitivity to therapeutic agents has revealed associations with p53 status and drug sensitivity. Recently, inventors identified the arginine-serine (RS) rich domain as the minimal core region of SMAR1 that is responsible for activating p53-mediated pathway. In the present study, inventors investigated the antitumorigenic activity of a 33 amino-acid peptide sequence corresponding to the RS domain of SMAR1. The peptide was conjugated to protein transduction domain (PTD) of HIV-1 Tat protein, (TAT-SMAR1 WT peptide; p44) as PTD-TAT protein has been known to deliver bioactive peptides into tissues and across the blood-brain barrier. We found that almost 100% of cells were efficiently transduced by various SMAR1-derived peptides as observed through confocal imaging. All the chimeric TAT-SMAR1 derived peptides demonstrated efficient nuclear compartmentalization irrespective of the point mutations (PS347A-PS350A and SM) in the wild type SMAR1 peptide (P44), thereby suggesting that TAT PTD fusion with the SMAR1 peptide worked as an efficient peptide-delivery system. The P44 minimal peptide sequence of SMAR1 retained the functional activity of the full-length SMAR1 as it was capable of activating p53 as well as retaining into the nucleus. Accumulation of p53 in the nucleus resulted into arrest of the cell cycle at G2/M phase, which is in accord with the known growth inhibitory properties of high levels of wild-type p53.

Interestingly, the microarray data also demonstrated down regulation of important cell cycle regulatory proteins. Genes involved in regulating mitosis, MAPK signaling and cell cycle checkpoints showed significant decreased expression upon P44 treatment, emphasizing its role as a cell cycle modulator. Furthermore, reduced expression of proteins involved in ubiquitin-proteasome signaling may serve as an alternative mechanism to support P44-mediated stabilization and increased nuclear retention of p53.

Recent studies have proposed that phosphorylation of N-terminal amino acids of p53 contribute to its regulation by affecting the binding of co-activators and the negative regulator MDM2. These studies emphasize the significance of phosphorylation at serine 15, serine 20 or serine 37 residue of p53 in maintaining protein stability as well as transactivation properties. Interestingly, P44 peptide alone could mediate the phosphorylation of p53 at its serine 15 residue and in effect result in upregulation of the phospho-cdc2, indicating that p53-modulating activity of full-length SMAR1 resided entirely within the P44 peptide. Results obtained from luciferase reporter assays further confirmed the bioactivity of the SMAR1 derived peptide and demonstrated that it followed a p53-dependent p21-growth suppression pathway. We have previously demonstrated that the substrate motif for protein kinase C family of serine threonine kinases resides within the arginine-serine rich domain of SMAR1. In this study, by using various point-mutated peptides of P44, it was demonstrated that serine 347 residue of SMAR1 is critical for its function and upon mutation to alanine (in case of PS347A as well as SM-mutant peptide), results in loss of its phosphorylation and hence reduced functional activity. However, staurosporine treatment resulted in a complete inhibition of phosphorylation of peptides containing intact serine 347 residue. Peptides where serine 347 was replaced with alanine (that included PS347A as well as SM) demonstrated no difference in their phosphorylation status irrespective of the presence or absence of STS, thereby emphasizing the importance of serine 347 in phosphorylation of P44 peptide. Moreover, in SM peptide wherein serine 347-350 residues were mutated to alanine, we observed further reduction in its phosphorylation compared to PS347A peptide, thus suggesting the significance of other serine, residues (348-350) in the phosphorylation of P44 peptide.

In this study using xenograft tumor nude mice model, it was demonstrated that the TAT-SMAR1 WT (P44) peptide strongly regressed tumors and the anti-tumorigenic activity of the P44 peptide was significantly reduced when the serine residues were mutated to alanine [TAT-SMAR1 RS mutant (SM)]. Histopathological analysis of tumor section from control tumors (TAT PTD and SM-treated) revealed increased cellular proliferation resulting into blood vessel condensation. However, there was pronounced destruction of the tumor architecture upon treatment with P44 peptide. It prevented vascular damage and maintained cellular integrity. Protection against hypoxia in solid tumours is an important step in tumour development and progression. A multifaceted adaptive response is triggered by hypoxia, which is primarily mediated by hypoxia inducible factor-1 (HIF-1) system, which plays a crucial role especially in angiogenesis and carcinogenesis. Alteration and overexpression of HIF-1α has been detected in a variety of solid tumours, including breast, lung, ovarian and oral cancer with varying staining patterns. We also observed an increased expression of HIF-1α in cells treated with either TAT PTD or SM peptide compared to those treated with P44 peptide. Thus, P44 peptide restores normoxia in tumor cells, which may be responsible for decreasing HIF-1α expression, even though the mechanism is yet not clear.

DETAILED DESCRIPTION OF THE FIGURES

FIG. 1. Cellular uptake of TAT conjugated SMAR1 derived peptides in HEK 293 cells. $2 \times 10^5$ cells were incubated with 10 μM concentration of peptide for 6 h at 37° C. Peptides were labeled with the TRITC-fluorochrome as described under "Experimental Procedures". A, A cartoon representation of the TAT PTD-SMAR1 chimeric peptide depicting its various domains. FIG. B corresponds to unconjugated SMAR1 peptide; C, TAT-SMAR1 WT (P44) peptide and D-H, various P44 serine mutant peptides (D, SM;E, PS347A; F, PA348A; G, PS349A; and H, PS350A) at a concentration of 10 μM. FIGS. I-L demonstrate dose-response study of TRITC-labeled P44 peptide. $2 \times 10^5$ 293 cells were incubated with varying concentration of peptide for 6 h at 37° C. FIG. I, 100 nM; J, 1 μM; L, 50 μM of the peptide concentration. Left panel shows the nuclear staining with DAPI, middle panel corresponds to TRITC fluorescence and the right panel shows a merged image. All images were recorded with the same camera acquisition parameters.

FIG. 2. P44 peptide activates the p53-driven p21 gene expression in reporter assays. p21 promoter activity was checked in both HEK 293 ($p53^{+/+}$) (A) and K562 ($p53^{-/-}$) cells (B). Cells were transfected with either pG13 CAT reporter plasmid, a p53-driven p21 promoter, in HEK 293 cells or cotransfected with wild-type (wt) p53 in K562 cells. After 24 h post-transfection, cells were treated for 12 h with 10 μM concentration of various TAT-SMAR1 chimeric peptides. Y axis represents the fold luciferase activity (mean±SD of three independent experiments).

FIG. 3. P44 peptide activates p53-mediated cell cycle pathway. A, HEK 293 cells were seeded at a density of $5 \times 10^5$ and after 24 h, was incubated with increasing concentrations of the TAT-SMAR1 WT (P44) peptide. Protein lysates were prepared and then immunoblotted with antibodies to total p53, phospho serine-15. B, The same set of experiment was repeated with TAT PTD peptide representing the PTD carrier sequence alone and immunoblotted with phospho serine-15, in comparison of P44 treated cells. C, The status of phospho cdc-2 was further analyzed in P44 peptide treated cells. Total ERIC was used as an internal control. D, The same set of experiments were again repeated using TAT-SMAR1 RS mutant (SM) peptide and whole cell lysates were probed for phospho p53 serine-15 and pcdc-2 antibodies. Action was used as a loading control.

FIG. 4. Serine 347 residue of SMAR1 mediates p53 activation and stabilization. A, HEK 293 cells were cultured at a density of $5 \times 10^5$ cells and 24 h later treated with 10 μM concentration of either the P44 or various serine-mutant peptides (PS347A, PS348A, PS349A, PS350A and RS mutant; SM). After 12 h of treatment, protein lysates were prepared and immunoblotted using pSer-15 p53 and pcdc-2 antibodies. Actin was used as the loading control. B, Peptides P44 (panel B), PS347A (panel C), PS348A (panel D), PS349A (panel E), PS350A (panel F) and SM (panel G) were incubated at a final concentration of 10 μM with HEK 293 cells for 12 h before indirect immunofluorescence detection with a primary antibody against p53 protein and a secondary fluorescein-conjugated anti-mouse IgG.

FIG. 5. Serine 347 residue of SMART is phosphorylated by protein kinase C. One microgram of various TAT-SMAR1 derived peptides (P44, PS347A, PS348A, PS349A, PS350A and SM) were subjected to an in vitro phosphorylation assay using whole cellular extract from HEK 293 cells and then the $\gamma$-$P^{32}$ ATP incorporation was detected as counts per minute by the scintillation, counter. Cells were either kept untreated (dark bars) or were treated with the PKC inhibitor, staurosporine at a final concentration of 20 nM (light bars).

FIG. 6. Tumor regression by TAT-SMAR1 WT peptide. A, Nude mice were allowed to develop tumors by subcutaneously injecting B 16F1 mouse melanoma cells. Mice with size-matched tumors were then randomized into three treatment groups (five animals per group); TAT PTD alone (panel A), TAT-SMART RS mutant (SM) (panel B) and TAT-SMAR1 WT (P44) (panel C). Panels D, E and F correspond to the magnified images of panels A, B and C, respectively. Mice were treated with either of the peptides at a dose of 200 μg/mice/thrice a week for consecutive 4 weeks. The tumors were then weighed and plotted for each mouse in all the treatment groups (panel G).

FIG. 7. Histopathological changes in B16F1-induced tumors. A, Hematoxylin and eosin staining of tumor sections excised from mice treated with either P44 (upper panel) or SM (lower panel) peptide. Vascular damage was observed in tumors treated with the mutant peptide; SM (arrows, lower right panel) whereas the blood vessels were relatively undamaged in the mice treated with the wild type peptide; P44 (arrows, upper right panel). The images have been recorded at 20× and 40×. B, Immunohistochemistry of paraffin embedded tumor sections from P44 treated as well as, SM treated mice. After antigen unmasking, sections were stained with HIF-1α antibody (middle panel) and detected using Cy-3 conjugated mouse immunoglobulin. Sections were counterstained with DAP1 for nuclear localization (left panel). Right panel corresponds to the merged image.

Table 1. Amino acid sequences of protein transduction domain and SMAR1 derived chimeric peptide conjugates. The chimeric peptides have SEQ ID NOs: 1-14, reading from the top to the bottom of the Table.

EXAMPLES

Peptide synthesis: The chimeric TAT-SMAR1 peptides [SMAR1 WT. (P44); SMAR1 RS mutant (SM); and other serine-mutant peptides (PS347A, PS348A, PS349A, and PS350A)] (Table 1) were custom synthesized from GenoMachanix, L.L.C. U.S.A. Peptides were resuspended in deionized water and stored at −20° C. until further use.

Labeling of SMAR1 peptides with TRITC fluorochrome: Twenty five microgram of the TAT-SMAR1 derived peptides dissolved in PBS was mixed with equimolar amount of 0.1M di-sodium tetraborate buffer, pH 9.0. This mixture was then incubated for 45 min in the dark at room temperature with 10 µg TRITC (5 mg/ml stock solution) dissolved in DMSO. The reaction was stopped by adding of 1M Tris glycine. The peptide-TRITC conjugate was loaded on the top of a PD-10 column (BioRad) that was previously equilibrated with PBC. The column was eluted with 10 ml of PBS and the first few fractions of the fluorescent material were collected. The LTV absorbance for the labeled peptide was measured at 550 nm (TRITC) and 280 nm (peptide).

Western blotting and immunoprecipitation: HEK 293 cells ($5 \times 10^5$) were cultured as exponentially growing sub confluent monolayer on 35 mm plates in DMEM medium (Invitrogen) supplemented with 10% (v/v) fetal calf serum. After 24 h, cells were treated with varying concentrations of either of the TAT-SMAR1 derived peptides (Table 1). Cells were then incubated at 37° C. for 12 h followed by preparation of whole cell protein extracts. For Western blotting, equal amount of the protein was separated on 10% SDS PAGE and subsequently transferred to PVDF membrane (Amersham). It was finally probed with the following antibodies; anti-p53 (DO-1); anti-phospho p53 Ser-15 and anti pcdc-2. The detailed protocol for the same is discussed in our earlier publication (30).

Immunocytochemistry and confocal imaging: For direct detection of TRITC-labeled peptides, HEK 293 cells were plated directly on a glass coverslip and cultured overnight prior to their treatment to TRITC-conjugated various TAT-SMAR1 derived peptides. After 12 h incubation, three washings with cold PBS were given and the cells fixed with 3.7% paraformaldehyde before being mounted in PBS/Glycerol (1:1) containing antifading agent. For indirect immunodetection, $2 \times 10^5$ HEK 293 cells were plated and cultured overnight in 35 mm plates on glass coverslips. The cell monolayer was then treated with either of the various TAT SMAR1 derived peptides, dissolved directly in complete DMEM medium at the appropriate concentration (final concentration 10 µM). After 12 h incubation, cells were washed twice with cold PBS and fixed with 3.7% paraformaldehyde. Subsequently, fixed cells were stained for total p53 using anti-p53 (DO-1) (SantaCruz) for an hour at room temperature.

For detection, cells were incubated with a secondary-antibody mix containing FITC-conjugated anti-mouse IgG antibodies (Sigma) for 1 h at RT. Slides were then mounted in antifade mounting medium (Dako) and analyzed with a confocal laser scanning microscope (CLSM 510, version 2.01; Zeiss, Thornwood, N.Y.).

Cell Cycle analysis by Flow Cytometry: HEK 293 cells were transiently transfected with GFP-tagged SMART truncations (160-288 aa and 288-350 aa). After 48 h of transfection, the cells were trypsinized, washed with 1× phosphate-buffered saline and fixed in 70% ice-cold ethanol. After incubating at −20° C. for 20 min, the cells were spun at 1000 rpm for 5 min at room temperature. The cells were washed with PBS, treated with RNase A (75 U/ml) for 30 min at 37° C., washed again in PBS and resuspended in PBS containing 50 µg/ml Propidium Iodide. After staining the cells with PI, they were analyzed by FACS Vantage (Becton Dickinson) using the cell quest program (Verity Software) for cell cycle profiles.

In vitro phosphorylation assay: HEK 293 cells were seeded at a density of $5 \times 10^5$ per well and harvested after 24 h either for preparation of whole cell extract or treatment with 20 nM concentration of staurosporine (a PKC inhibitor) (31, 32). After 48 h of treatment, lysates were prepared using the kinase lysisi buffer (20 mM Tris, pH 8.0, 500 mM NaCl, 1 mM EDTA, 1 mM EGTA, 10 mM β-Glycerophosphate, 10 mM NaF, 10 mM PNPP, 30 mM $Na_3VO_4$, 1 mM Benzamide, 2 mM PMSF, 1 mM DTT, 0.25% NP-40 and protease inhibitor cocktail). After incubating on ice for 20 min, lysates were spun at 14,000 rpm for 10 min. For the kinase reaction, various TAT-SMAR1 derived peptides (Table-1), were incubated with 2 µg of either the whole cell kinase extract (WCK) or with staurosporine-treated kinase extracts along with 10 µM ATP ($\gamma$-$P^{32}$), 2 mM $MgCl_2$ and the kinase assay buffer (20 mM Tris, 2 mM $MgCl_2$, 2 mM $CaCl_2$, 10 mM β-Glycerophosphate, 10 mM NaF, 10 mM PNPP, 30 mM $Na_3 VO_4$, 1 mM Benzamide, 2 mM PMSF, 1 mM DTT and protease inhibitor cocktail). The reaction mixture was incubated at 30° C. for 30 min and them reaction was stopped by adding 0.5 mM EDTA. BSA was added at a final concentration of 1 mg/ml along with 10% TCA. TCA-precipitated peptides were then resuspended in scintillation fluid and checked for $P^{32}$ incorporation.

Luciferase reporter assay: HEK 293 ($p53^{+/+}$) and K562 ($p53^{-/-}$) cells were grown in DMEM supplemented with 10% FBS in the presence of 5% $CO_2$ at 37° C., a total number of $1 \times 10^6$, cells were plated on a 6-well plate. After 24 h, cells were transiently transfected using lipofectamine-2000 with either 1 µg of p21 expression plasmid having luciferase reporter gene or 5 µg p21 luciferase along with wt p53 construct in K562 cell line. Two micrograms of pRL-CMV (Renilla luciferase reporter plasmid) was included in all transfections to normalize the transfection efficiency. Thirty six hours post-transfection, cells were treated with 10 µM of either P44 peptide or its various mutants. The cells were harvested 12 h post-treatment, washed with PBS and lysed in 1× Passive lysis buffer (Promega). After three freeze-thaw cycles, cells were spun at 10,000 rpm at 4° C. for 20 min. The supernatants were collected and protein concentrations were estimated spectrophotometrically using Bradford reagent as (BioRad, CA). According to the manufacturer's instructions, luciferase activity was assessed using the dual luciferase assay reporter kit (Promega). The luciferase activity was measured by using Fluoroskan Ascent Luminometer (Labsystems). For all the luciferase assays, the data shown are the mean+SD of three independent experiments.

Animal model for tumorgenesis: B16F1 mouse melanoma cells in the exponential growth phase were trypsinized (Invitrogen) and washed twice with PBS. Cell number and viability was assessed and cell cultures with viability >90% were used. Tumors were then established in nude mice by subcutaneous injection of $2 \times 10^6$ B16F1 cells. Five mice were used in each set of experiments. The mice were maintained under pathogen-free conditions. When the subcutaneous tumor was clearly visible, the TAT-SMAR1 WT (P44) peptide treatment was started. The P44 peptide was subcutaneously injected proximal to the tumor sites at a dose of 200 µg/mouse thrice a week. The treatment was administered for 4 weeks. For control treatment, TAT PTD alone and TAT SMAR1 RS mutant peptide (SM) were injected in the same manner as the P44 peptide.

Immunohistochemical staining of tumor sections: Tumor sections in paraffin-embedded blocks were transferred to poly-L-lysine coated glass slides and air-dried overnight at 37° C. They were dewaxed in xylene (three changes) and dehydrated in graded series of decreasing ethanol concentrations. After deparaffinization and rehydration, antigen retrieval was performed by immersing the slides in 10 mM sodium citrate buffer (pH 6.0) and subjected to microwave irradiation for 10 min. After antigen unmasking, a cooling-off period of 30 minutes preceded the incubation of the primary antibody (anti-HIF-1α; 1/100 dilution; SantaCruz). Thereafter, detected using cy-3 fluorescence labeled secondary antibody. All sections were counterstained with HE and dehydrated in alcohol and xylene. Tissue samples with non-immune serum served as negative controls.

| Peptide | Sequence (N–C) |
|---|---|
| TAT | YGRKKRRQRRR |
| TAT-SMAR1WT (P44) | YGRKKRRQRRRTAWRRKQRGQSLAVKSFSRRTPSSSSYSASETM |
| TAT-SMAR1 RS mutant (SM) | YGRKKRRQRRRTAWRRKQRGQSLAVKSFSRRTPAAAAYSASETM |
| Point mutants of P44 | |
| PS347A | YGRKKRRQRRRTAWRRKQRGQSLAVKSFSRRTPASSSYSASETM |
| PS348A | YGRKKRRQRRRTAWRRKQRGQSLAVKSFSRRTPSASSYSASETM |
| PS349A | YGRKKRRQRRRTAWRRKQRGQSLAVKSFSRRTPSSASYSASETM |
| PS350A | YGRKKRRQRRRTAWRRKQRGQSLAVKSFSRRTPSSSAYSASETM |
| PS1A | YGRKKRRQRRRTAWRRKQRGQSLAVKSFSRRTPSAAAYSASETM |
| PS2A | YGRKKRRQRRRTAWRRKQRGQSLAVKSFSRRTPSSAAYSASETM |
| PS1T | YGRKKRRQRRRTAWRRKQRGQSLAVKSFSRRTPTAAAYSASETM |
| PS2T | YGRKKRRQRRRTAWRRKQRGQSLAVKSFSRRTPTSSSYSASETM |
| PS3T | YGRKKRRQRRRTAWRRKQRGQSLAVKSFSRRTPTTTTYSASETM |
| PS5A | YGRKKRRQRRRTAWRRKQRGQSLAVKSFSRRTPAAAAYAASETM |
| PS5T | YGRKKRRQRRRTAWRRKQRGQSLAVKSFSRRTPAAAAYTASETM |

We claim:

1. A chimeric tumor suppressor activating peptide comprising 33 amino acids from the SMAR1 protein and an 11 amino acid protein transduction domain of the HIV-1 TAT protein, wherein the peptide is represented by the sequence (SEQ ID NO: 2)
YGRKKRRQRRRTAWRRKQRGQSLAVKSFSRRTP*SSSSY*SASETM,
or (SEQ ID NO: 5)
YGRKKRRQRRRTAWRRKQRGQSLAVKSFSRRTP*SA*SSY*SASETM,
or (SEQ ID NO: 6)
YGRKKRRQRRRTAWRRKQRGQSLAVKSFSRRTP*SSA*SY*SASETM,
or (SEQ ID NO: 7)
YGRKKRRQRRRTAWRRKQRGQSLAVKSFSRRTP*SSSA*Y*SASETM.

2. The chimeric peptide according to claim 1, wherein the sequence of the peptide is YGRKKRRQRRRTAWRRKQRGQSLAVKSFSRRTPSSSSYSASETM (SEQ ID NO:2).

* * * * *

SEQUENCE LISTING

<160> NUMBER OF SEQ ID NOS: 14

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 44
<212> TYPE: PRT
<213> ORGANISM: Artificial Sequence
<220> FEATURE:
<223> OTHER INFORMATION: Description of Artificial Sequence: Synthetic

```
                                polypeptide

<400> SEQUENCE: 2

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ser Ser Tyr Ser Ala Ser Glu Thr Met
        35                  40

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ala Ala Ala Ala Tyr Ser Ala Ser Glu Thr Met
        35                  40

<210> SEQ ID NO 4
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ala Ser Ser Ser Tyr Ser Ala Ser Glu Thr Met
        35                  40

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ala Ser Ser Tyr Ser Ala Ser Glu Thr Met
        35                  40

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 6

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ser Ala Ser Tyr Ser Ala Ser Glu Thr Met
        35                  40

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ser Ser Ala Tyr Ser Ala Ser Glu Thr Met
        35                  40

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ala Ala Ala Tyr Ser Ala Ser Glu Thr Met
        35                  40

<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ser Ser Ala Ala Tyr Ser Ala Ser Glu Thr Met
        35                  40

<210> SEQ ID NO 10
<211> LENGTH: 44
<212> TYPE: PRT
<213> ORGANISM: Artificial Sequence
<220> FEATURE:
<223> OTHER INFORMATION: Description of Artificial Sequence: Synthetic

```
                                   polypeptide

<400> SEQUENCE: 10

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Thr Ala Ala Ala Tyr Ser Ala Ser Glu Thr Met
        35                  40

<210> SEQ ID NO 11
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Thr Ser Ser Ser Tyr Ser Ala Ser Glu Thr Met
        35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Thr Thr Thr Thr Tyr Ser Ala Ser Glu Thr Met
        35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ala Ala Ala Ala Tyr Ala Ala Ser Glu Thr Met
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
```

```
                                 polypeptide

<400> SEQUENCE: 14

Tyr Gly Arg Lys Lys Arg Arg Gln Arg Arg Thr Ala Trp Arg Arg
1               5                   10                  15

Lys Gln Arg Gly Gln Ser Leu Ala Val Lys Ser Phe Ser Arg Arg Thr
            20                  25                  30

Pro Ala Ala Ala Tyr Thr Ala Ser Glu Thr Met
        35                  40
```